United States Patent
Zang et al.

(10) Patent No.: US 8,809,063 B2
(45) Date of Patent: Aug. 19, 2014

(54) FLUORESCENT CARBAZOLE OLIGOMERS NANOFIBRIL MATERIALS FOR VAPOR SENSING

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/806,538

(22) PCT Filed: Jun. 21, 2011

(86) PCT No.: PCT/US2011/041292
§ 371 (c)(1),
(2), (4) Date: Apr. 15, 2013

(87) PCT Pub. No.: WO2012/047330
PCT Pub. Date: Apr. 12, 2012

(65) Prior Publication Data
US 2013/0217139 A1 Aug. 22, 2013

Related U.S. Application Data

(60) Provisional application No. 61/357,015, filed on Jun. 21, 2010.

(51) Int. Cl.
| | |
|---|---|
| *G01N 33/22* | (2006.01) |
| *G01N 21/64* | (2006.01) |
| *G01N 33/00* | (2006.01) |
| *C07D 209/00* | (2006.01) |
| *C09K 11/06* | (2006.01) |
| *G01N 21/77* | (2006.01) |

(52) U.S. Cl.
CPC .......... *G01N 21/643* (2013.01); *G01N 33/0057* (2013.01); *C09K 2211/1029* (2013.01); *G01N 21/64* (2013.01); *G01N 2021/7786* (2013.01); *C07D 209/00* (2013.01); *C09K 11/06* (2013.01)
USPC ............. 436/106; 436/96; 436/111; 436/164; 436/167; 436/172; 436/181; 422/82.05; 422/82.08; 422/83; 422/88; 422/91; 422/94

(58) Field of Classification Search
USPC ........... 436/96, 106, 111, 164, 167, 172, 181; 422/400, 82.05, 82.08, 83, 88, 91, 94
See application file for complete search history.

(56) References Cited

U.S. PATENT DOCUMENTS 6,528,657 B2 * 3/2003 Nakaya et al. ................. 548/440
7,605,327 B2 10/2009 Roscheisen et al.
(Continued)

FOREIGN PATENT DOCUMENTS

WO WO 2005/016882 2/2005

OTHER PUBLICATIONS

Naddo, et al.; "Highly responsive fluorescent sensing of explosives taggant with an organic nanofibril film"; Sensors and Actuators B: Chemical, 2008, vol. 134, Issue 1, pp. 287-291.
(Continued)

*Primary Examiner* — Maureen Wallenhorst
(74) *Attorney, Agent, or Firm* — Thorpe North & Western LLP

(57) ABSTRACT

A fluorescence based sensor (10) is disclosed and described. The sensor (10) can include nanofibril materials (12) fabricated from a linear carbazole oligomer and a fluorescence detector (14). The linear carbazole oligomer can have the formula (I) wherein n is 3 to 9, R are independently selected amine sidegroups, and at least one, but not all, R is a C1 to C14 alkyl. The carbazole-based fluorescence based sensors (10) can be particularly suitable for detection of explosives and volatile nitro compounds.

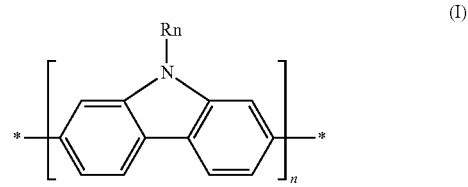

(I)

22 Claims, 8 Drawing Sheets

(56) References Cited

U.S. PATENT DOCUMENTS

| | | | |
|---|---|---|---|
| 8,153,065 B2* | 4/2012 | Zang et al. | 422/82.08 |
| 8,431,708 B2* | 4/2013 | Chang et al. | 546/193 |
| 2003/0092880 A1 | 5/2003 | Leclerc et al. | |
| 2005/0150778 A1 | 7/2005 | Lewis et al. | |
| 2009/0233374 A1 | 9/2009 | Zang et al. | |
| 2012/0288950 A1* | 11/2012 | Zang et al. | 436/106 |
| 2013/0065319 A1* | 3/2013 | Zang et al. | 436/104 |

OTHER PUBLICATIONS

Ling Zang, et al.; One Dimensional Self-Assembly of Planar π Conjugated Molecules: Adaptable Building Blocks for Organic Nanodevices; Departments of Chemistry and Materials Science and Engineering, University of Illinois at Urbana—Champaign, Urbana, IL 61801; Received on Jan. 31, 2008.

Yanke Che, et al.; "Ambient Photodoping of p-Type Organic Nanofibers: Highly Efficient Photoswitching and Electrical Vapor Sensing of Amines"; Chem. Commun.; 2010, 46, 4127-4129.

Che, et al.; "Expedient Vapor Probing of Organic Amines Using Fluorescent Nanofibers Fabricated from an n-Type Organic Semiconductor"; Nano Letters 2008; vol. 8, No. 8, 2219-2223.

Che, et al.; "Ultralong Nanobelts Self-Assembled from an Asymmetric Perylene Tetracarboxylic Diimide"; J.Am.Chem.Soc. 2007, vol. 129; pp. 7234-7235.

Kim, et al.; "Charge mobilities and luminescence characteristics of blue-light emitting bent carbazole trimers connected through vinylene likers—effect of nitrile substituents"; Synthetic Metals vol. 145; 2004; p. 229-235.

Maruyama, et al.; "The photoluminescent and electroluminescent properties of cyclic carbazole oligomers"; Phys. Chem. Chem. Phys. 2000; vol. 2; pp. 3565-3569.

Naddo, et al.; "Detection of Explosives with a Fluorescent Nanofibril Film"; 2007 American Chemical Society; vol. 129; pp. 6978-6979.

Sonntag, et al.; "Novel 2, 7-Linked Carbazole Trimers as Model Compounds for conjugated Carbazole Polymers"; Chem. Mater. 2004, vol. 16, pp. 4736-4742.

Zang, et al.; "Orangic nanofibrils based on linear carbzole trimer for explosive sensing"; Chem. Commun , 2010, vol. 46, pp. 5560-5562; published on the web Jun. 24, 2010.

Zhang, et al.; "A Novel Approach to the Synthesis of Conjugated Carbazole Trimers as Multifunctional Chromophores for Photorefractive Materials"; Tetrahedron Letters, vol. 38, No. 10; pp. 1785-1788; 1997.

Zhang, et al.; "Amorphous conjugated Carbazole Trimers for Photorefractive Materials"; Chem. Mater. 2798-2804; vol. 9, 1997.

* cited by examiner

FLUORESCENT CARBAZOLE OLIGOMERS NANOFIBRIL MATERIALS FOR VAPOR SENSING

GOVERNMENT INTEREST

This invention was made with government support under Grants No. CBET0730667 and No. CHE0641353 awarded by the National Science Foundation and Award No. 2009-ST-108-LR0005 awarded by the U.S. Department of Homeland Security. The Government has certain rights in the invention.

BACKGROUND

Detection of trace explosives is of great concern for the homeland security, battlefield protection, and industrial and environmental safety control. Fluorescence quenching based sensing has proven to be one of the most promising approaches for trace explosives detection, for which various conjugated polymers, molecular imprinted polymers, dye-doped silica and metal-organic frameworks have been fabricated into films. Fluorescence quenching of these materials upon exposure to vapors of nitroaromatic explosives (e.g., TNT, DNT) has been explored. However, the quenching efficiency of these materials is often limited by short exciton diffusion due to the poor molecular organization and/or weak intermolecular electronic interactions as usually observed for polymer based materials. As a result, reliable results for very low concentrations can be difficult to achieve and sensitivity can be limited.

Recently, an alternative approach to increase fluorescence sensing efficiency by fabricating rigid aromatic molecules into nanofibrils has been reported. These novel one-dimensional nanostructures possess long range exciton diffusion due to the extended intermolecular $\pi$-$\pi$ electronic interaction. Upon deposition onto a substrate, the nanofibrils form a nanoporous film in a variable range of porosity through entangled piling of the individual fibrils. The large surface area to volume ratio and porosity thus formed, in combination with the amplified fluorescence quenching relied on the enlarged exciton diffusion, usually enable expedient, effective vapor detection of nitroaromatic explosives. Particularly, for the building-block molecules containing carbazole as the conjugation unit, the nanofibrils thus fabricated demonstrate not only high sensitivity in vapor sensing, but also strong selectivity towards nitrobased explosives against other common chemical liquids and solids. However, the macrocyclic conjugation structure of these molecules imposes significant difficulty during synthesis because synthesis of these macrocyclic demands special catalysts for making the precursors. Consequently, these materials are currently limited in practical application due at least in part to these difficulties. To make the nanofibrils more practical in vapor sensing, the inventors determined to find alternative building-block molecules that are easier to synthesize but still maintain the chemical properties and features suited for fabrication into nanofibrils and fluorescence sensing of nitrobased explosives.

SUMMARY

A fluorescence based sensor can include nanofibrils fabricated from a linear carbazole oligomer and a fluorescence detector. The linear carbazole oligomer can have the formula

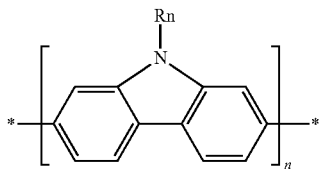

where n is 3 to 9, Rn are independently selected amine sidegroups, and at least one Rn is a C1 to C14 alkyl. The amine sidegroups can be any suitable sidegroups which provide desired morphology of the detection material and does not interfere with association with a target sample.

The fluorescence base sensors and materials can be readily used to detect target samples, and are especially effective at detecting explosives. Accordingly, a method of detecting explosives can include exposing a linear carbazole oligomer to a target sample, the linear carbazole oligomer having the formula

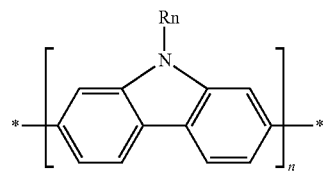

where n is 3 to 9, Rn are independently selected amine side groups, and at least one Rn is a C1 to C14 alkyl. These groups and variables can be chosen as described previously. Fluorescence responses of the linear carbazole oligomer can then be measured.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
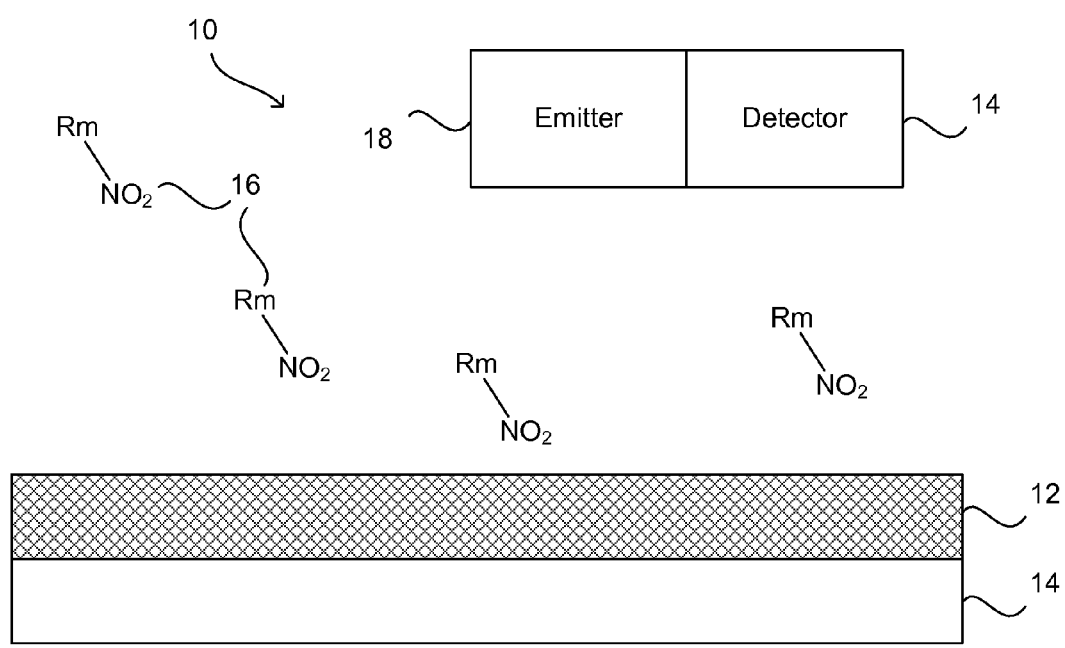
FIG. 1 is a schematic of a fluorescence based sensor using the nanofibrils described herein and nitro based target compounds.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a nanofibril" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Referring to FIG. 1, a fluorescence based sensor 10 can include nanofibrils 12 fabricated from a linear carbazole oligomer, and a fluorescence detector 14. The linear carbazole oligomer can have the formula

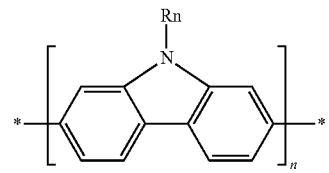

where n is 3 to 9, Rn are independently selected amine sidegroups, and at least one Rn is a C1 to C14 alkyl. The carbazole provides a linear backbone to the oligomer chain having single bonds between each carbazole unit. The single bonds allow the individual carbazole units to rotate with respect to one another. The number of carbazole units can vary from 3 to 9, although is often 3 to 5 units. Longer oligomer chains tend to be insoluble in common solvents due at least partially to the extended π-conjugation length and thus can be difficult to assemble them into uniform nanofibers. Moreover, longer oligomer chains bring forward more challenging synthesis steps. In contrast, shorter oligomer chains tend to be more soluble in common organic solvent and consistently form nanofibrils and easily synthesizable. In one aspect, the carbazole can be free of any non-amine side groups (i.e. groups attached around the carbazole ring).

The amine sidegroups Rn can be any suitable sidegroups which provide the desired nanofibril morphology of the detection material 12 and does not interfere with association of the nanofibril material with a target sample 16. Although not required, the amine side groups generally include different types of moieties on a portion of the carbazole core units such that not all Rn are the same within the oligomer. In one alternative, at least one Rn is selected from the group consisting of linear alkyl, branched alkyl, cyclic alkyl, and combinations thereof. As a general guideline, Rn can have about 0 to about 16 carbons. Smaller side groups tend to be insoluble in common solvents, while larger side chains tend to be soluble. In one specific aspect, the at least one Rn is octyl. Alternatively, the Rn are chosen such that fewer than half are selected from linear alkyl, branched alkyl, cyclic alkyl, and combinations thereof while the remainder are hydrogen. In such cases, at least one Rn can be selected from H and other groups which do not interfere with formation of nanofibrils.

Although not entirely understood, it appears that interactions of electron-donating carbazole moiety with the electron-accepting nitro-groups of the explosives provide binding with the nanofibril materials.

In one specific example, n can be 3. In another even more specific example, R1 is H, R2 is octyl and R3 is H such that the linear carbazole oligomer is

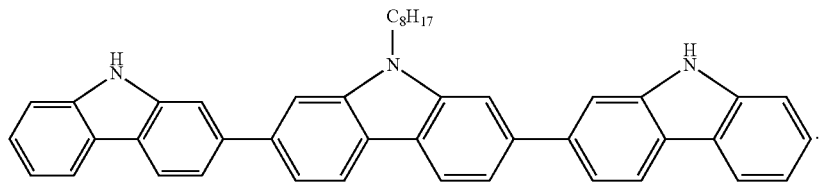

The morphology of the linear carbazole oligomer can be a function of the length of the oligomer and the amine side-groups. For example, longer oligomers, such as those with n>9, are difficult to assemble into uniform nanofibers due to poor solubility in common solvents. In one aspect, the linear carbazole oligomer can be a nanofibril. Typically, although not exclusively, nanofibrils can be about 10 nm to about 100 nm in diameter, and often about 25 nm to about 35 nm.

A nanofibril film can be oriented on a suitable mechanical substrate for use in a sensor. Any mechanical substrate can be used, as long as the material does not damage or inhibit vapor sensing of the oligomer. The nanofibrils 12 can be provided as a mass formed in any suitable shape. Non-limiting examples can include a coating, film, block or the like. In one aspect, the linear carbazole oligomer is formed as a film of nanofibrils. The nanofibrils can be formed as a thin film through which vapors can be passed or which is placed adjacent a support substrate 14. In such configurations, the film can generally range from about 0.1 μm to about 50 μm in thickness, although from about 0.5 μm to about 10 μm can be useful for some applications. As mentioned, the nanofibrils can be associated or deposited on a support substrate 14. The support substrate can be a solid layer or can be a porous material such as a porous solid or ceramic or polymer beads. Non-limiting examples of suitable substrates can include glass, metals, polymers, and the like. Substrates can be chosen to avoid degradation of the nanofibril material and not adversely affect fluorescence performance of the material. Further, porous support materials can be coated with the nanofibril materials to provide additional surface area for detection and sensitivity within a reduced sensor size. For example, zeolites, ceramics, aerogels, zerogels, and other porous materials can be used. In yet another option, the nanofibril material can be supported by a circumferential frame which suspends the nanofibril material as a sheet or film across a passage. In this manner, air or other gases can be passed through the nanofibril material allowing for increased volumetric flow past the nanofibrils.

The linear carbazole oligomer can be oriented such that a fluorescence detector 14 can be used to detect changes in fluorescence upon association with a target sample 16 (e.g. explosive vapor or gas). The fluorescence sensor can often be a fluorimeter or photomultiplier tube (PMT). As such, the sensor device can avoid using electrodes or other electrical conductors associated with the nanofibril layer. This is due to the fluorescence mechanism used which relies on the emission of an exciting radiation such as from a UV emitter 18 or other radiation source. The nanofibril materials exhibit distinct fluorescence changes upon exposure to specific target samples 16 which can be detected by the fluorescence detector 14.

Although not required, a suitable housing can be used to provide a convenient mechanism for use by technicians, security or other persons. The housing can include an opening which allows passage of air which is suspected of containing target sample vapors. The opening can be in fluid communication with the nanofibril material housed within the housing. The fluorescence detector 14 can be oriented in visible communication range of the nanofibril material 12. An optional emitter 18 can be provided to excite fluorescence within the nanofibril material as explained herein. An indicator can also be used to communicate presence and/or absence of fluorescence to a user. The indicator can include a display which is viewable by a user such as through an opening in the housing. For example, a simple light indicator can be illuminated when a threshold fluorescence is reached indicating presence of a target sample material. Alternatively, the indicator can provide a more quantitative value such as a numerical reading based on an arbitrary scale (e.g. 0-10) or specific fluorescence measurement as reported by the fluorescence detector. Other indicators can be used based on the desired application (e.g. laboratory measurement would generally require quantitative readings while security may be more qualitative readings).

The above sensors and materials can be readily used to detect target samples, and are especially effective at detecting explosives. The binding chemistry is particularly effective at association with nitoaliphatic and nitroaromatic explosives, although other compounds such as quinones can be detected. Accordingly, a method of detecting explosives and quinones can include exposing a linear carbazole oligomer to a target sample, said linear carbazole oligomer having the formula

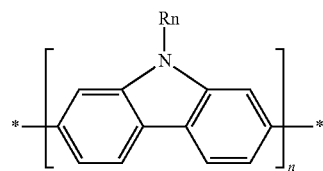

where n is 3 to 9, Rn are independently selected amine side-groups, and at least one Rn is a C1 to C14 alkyl. These groups and variables can be chosen as described previously. Fluorescence responses of the linear carbazole oligomer can then be measured.

An explosives indicator can be displayed based on the fluorescence responses. For example, the explosives indicator can be a quantitative measurement (such as a digital numerical readout). Alternatively, the explosives indicator can be a qualitative measurement (e.g. color change, light signal, or other positive indicator).

The target sample can be any volatile vapor or gas which associates with the oligomer. Non-limiting examples of target samples can include nitroaromatic explosives and nitroaliphatic explosives which include a nitro group and are generally represented as $Rm\text{-}NO_2$, where Rm is either an aromatic or aliphatic group. Nitroaromatic explosives can include, but are not limited to, 2,4,6-trinitrotoluene (TNT), dinitrotoluene (DNT), 1,3,5-trinitrobenzene (TNB), 1,3-dinitrobenzene (DNB), 1,3,5-trinitroperhydro-1,3,5-triazine (RDX), mononitrotoluene (MNT), picric acid (PA) and the like. Nitoaliphatic explosives can include, but are not limited to, pentaerythritol tetranitrate, ethylene glycol dinitrate (EGDN), tetranitromethane, nitromethane, nitroethane, nitroglycerin, 2-nitropropane, pentaerythritol tetranitrate (PETN), and the like.

Advantageously, the nanofibril materials described herein can be readily regenerated as the binding with target samples is highly reversible. Bonded materials can be regenerated by moderate heating sufficient to drive off the bonded target materials. For example, heating at temperatures from about 20° C. to about 70° C. (such as about 50° C.) for a period of time can be sufficient. Although a few minutes is usually sufficient, up to 8 minutes or more can be used to ensure complete removal of the bonded target materials. Further, heating can often be performed under vacuum to prevent adverse reaction of the nanofibrils or target materials with other compounds.

The methods and materials can be highly sensitive to relatively low concentrations of target sample. In one aspect, the fluorescence responses can be statistically significant at target sample concentrations of about 5 ppb and greater, and in some case 350 ppm and greater.

Examples

Synthesis of a 2,7-linked carbazole trimer is shown in Scheme 1 below and fabrication into nanofibril structures was performed. A nanofibril film thus fabricated demonstrated efficient, fast fluorescent sensing not only for nitroaromatic explosives (e.g., TNT, DNT), but also for nitroaliphatic explosives (e.g., nitromethane), which remain difficult to detect due to their high volatility and low chemical binding to many sensory materials.

The carbazole trimer was synthesized from commercially available 2,7-dibromo-9-octyl-9H-carbazole and 9H-carbazole-2-boronic acid pinacol ester in one step by Suzuki-coupling reaction (Scheme 1). The 2,7-substituted carbazoles, compared to 3,6-substituted ones, are ideal building blocks for rigid, rodlike molecules with a longer conjugation distance. Introducing one octyl substituent gives the trimer solubility for solution processing while maintaining minimal steric hindrance to facilitate the intermolecular arrangement and one-dimensional self-assembly into nanofibrils. Indeed, well-defined nanofibrils can be fabricated from this molecule through a bisolvent phase transfer process as described below. In comparison, when substituting all the three carbazoles with long alkyl chains (e.g. octyl), the self-assembly through the same process gave only ill-defined big chunks.

Scheme 1: Synthesis of 2,7-linked carbazole trimer

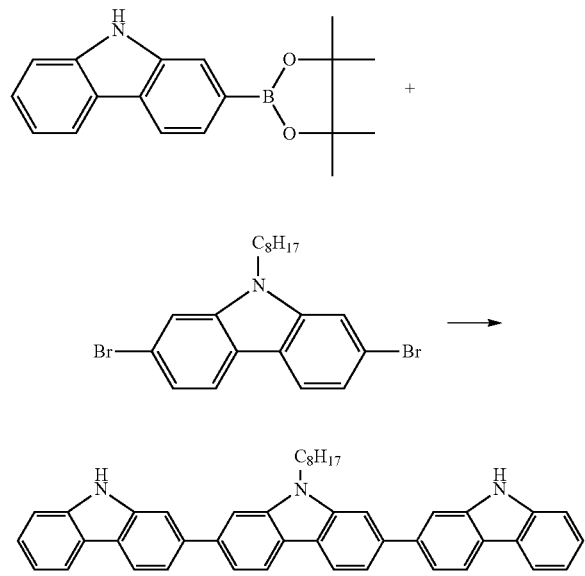

Synthesis of the Carbazole Trimer:

A solution of 2,7-dibromo-9-octyl-9H-carbazole (220 mg, 0.5 mmol), 9H-carbazole-2-boronic acid pinacol ester (880 mg, 1.5 mmol) and benzyltriethylammonium chloride (50 mg) in a mixture of toluene (20 mL) and aqueous $K_2CO_3$ (2M, 8 mL) was degassed by three freeze-pump-thaw cycles. $Pd(PPh_3)_4$ (5 mg) was added under argon and degassed by three freeze-pump-thaw again. The mixture was refluxed for 24 h and the organic phase was separated and evaporated. The product was purified by column chromatography (hexane/THF, 4:2) and dried in vacuum. A 220 mg (71%) yield of trimer carbazole was obtained as a light brown powder. $^1$H NMR (THF-d8, 500 MHz): δ=10.33 (s, 2H), 8.15 (m, 4H), 8.07 (d, J=7.9, 2H), 7.82 (m, 4H), 7.6 (m, 4H), 7.43 (d, J=8.0, 2H), 7.34 (m, 2H), 7.15 (m, 2H), 4.56 (t, J=7.19, 2H), 1.99 (m, 2H), 1.29 (m, 10H), 0.83 (t, J=6.9, 3H). MALDI-TOF MS: m/z 609.33 (100%).

Fabrication of Nanofibril Films:

An amount of 0.5 mL carbazole trimer solution (0.5 mM, in tetrahydrofuran) was dropped into 3 mL of hexane while stirring. A white floc (entangled nanofibrils) was formed immediately and suspended in the solution. To fabricate the nanofibril films, one drop of the nanofibril solution was cast onto a glass slide or silicon substrate, followed by drying in a vacuum oven for 30 minutes.

UV-vis absorption spectra and fluorescence spectra were measured on a PerkinElmer Lambda 25 spectrophotometer and LS 55 fluorometer, respectively. Fluorescence microscopy imaging was carried out with a Leica DMI4000B inverted microscope, with excitation at 365 nm. SEM measurement was performed with a FEI NanoNova 6300 microscope, and the samples were directly drop-cast on a silica substrate. X-ray diffraction was carried out with a Philips X'Pert XRD instrument. The fluorescence quenching by explosive vapor was monitored.

Figure 2A:
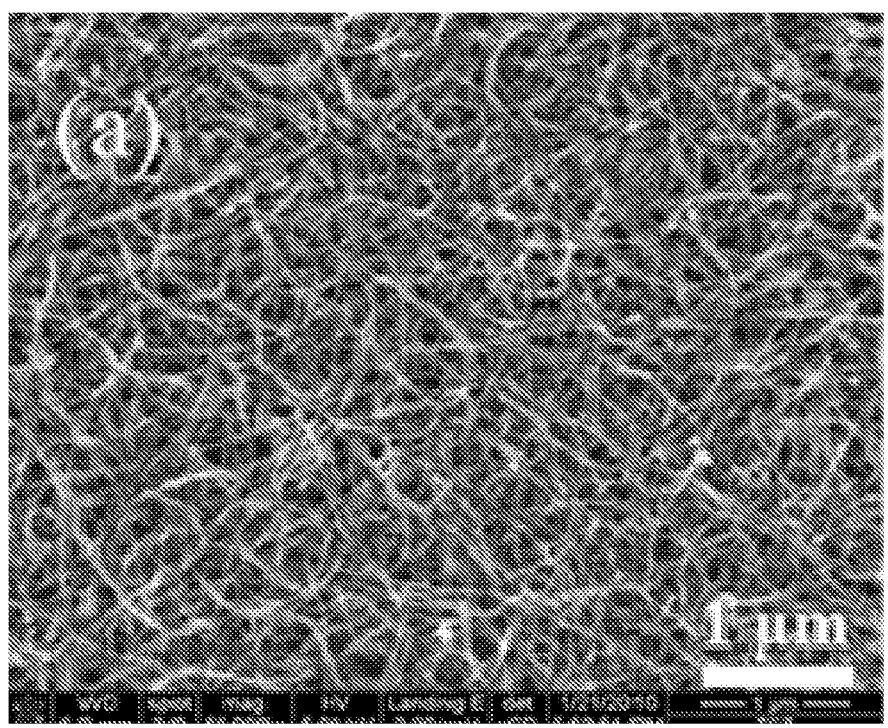
FIG. 2A is an SEM image of nanofibrils deposited on a silicon substrate.
Figure 2B:
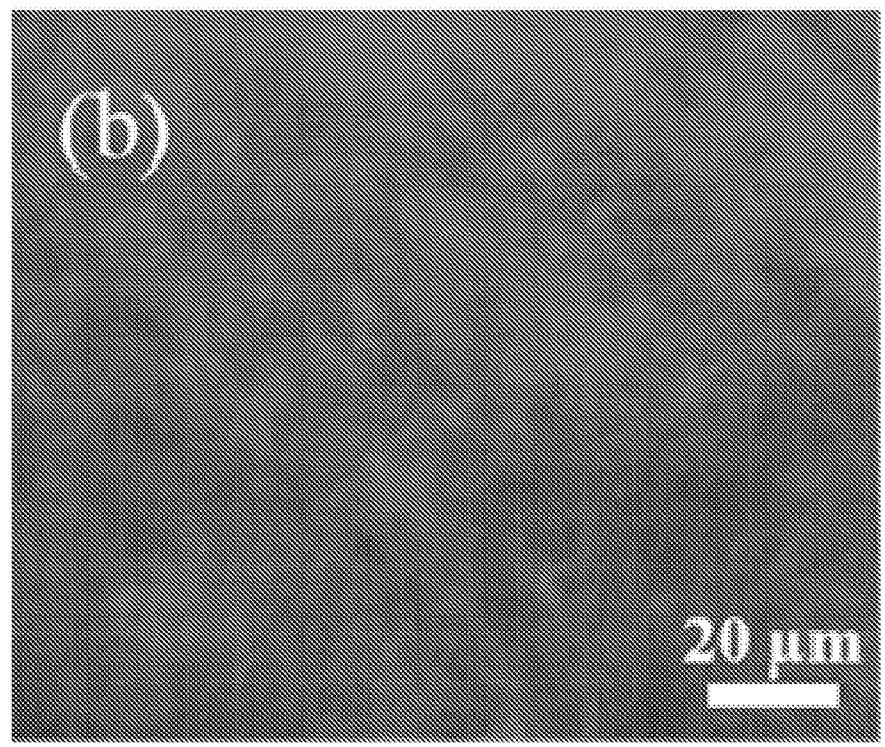
FIG. 2B is a fluorescence microscopy image of the same nanofibrils deposited on a glass slide.
Figure 3:
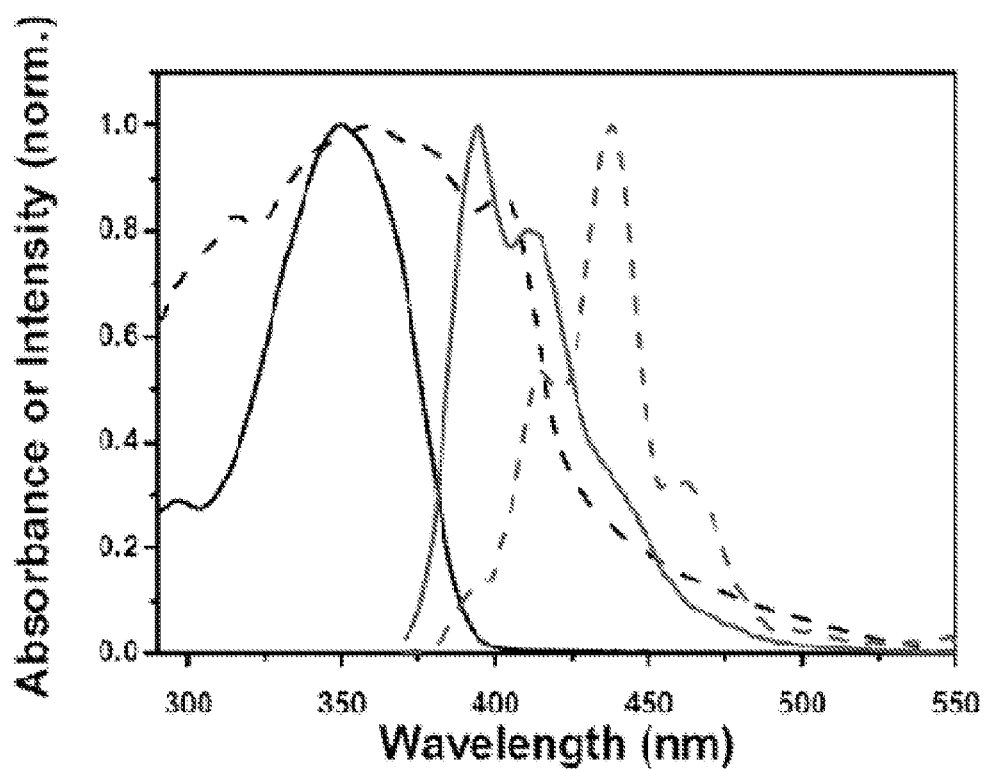
FIG. 3 shows the absorption (black) and fluorescence (red) spectra of the carbazole trimer in tetrahydrofuran solution (5 µM, solid) and nanofibril film deposited on glass (dashed). The fluorescence spectra were excited at 350 nm.

Results:

FIG. 2A shows a SEM image of the nanofibrils fabricated from the carbazole trimer deposited on a silicon substrate. The nanofibrils feature a high aspect ratio, with diameter of only ca. 30 nm and length of several microns. The deposited nanofibrils formed a nanoporous film consisting of entangled fibril networks. The nanofibrils exhibit strong blue fluorescence upon excitation under UV light as shown by fluorescence microscopy imaging (FIG. 2B). Although the figure is provided in gray-scale, lighter areas show as pale light blue while darker areas show as dark blue to almost black when viewed in color. The maximum wavelength of the fluorescence and absorption was measured at 438 nm and 402 nm, respectively, 44 nm and 55 nm longer than those measured for the molecules dissolved in solution (FIG. 3), which is characteristic of strong intermolecular electronic interaction typically observed in molecular aggregates. Such strong intermolecular interaction is also indicated by the bathochromic shifted absorption peak (around 400 nm) as measured for the nanofibrils.

Figure 4A:
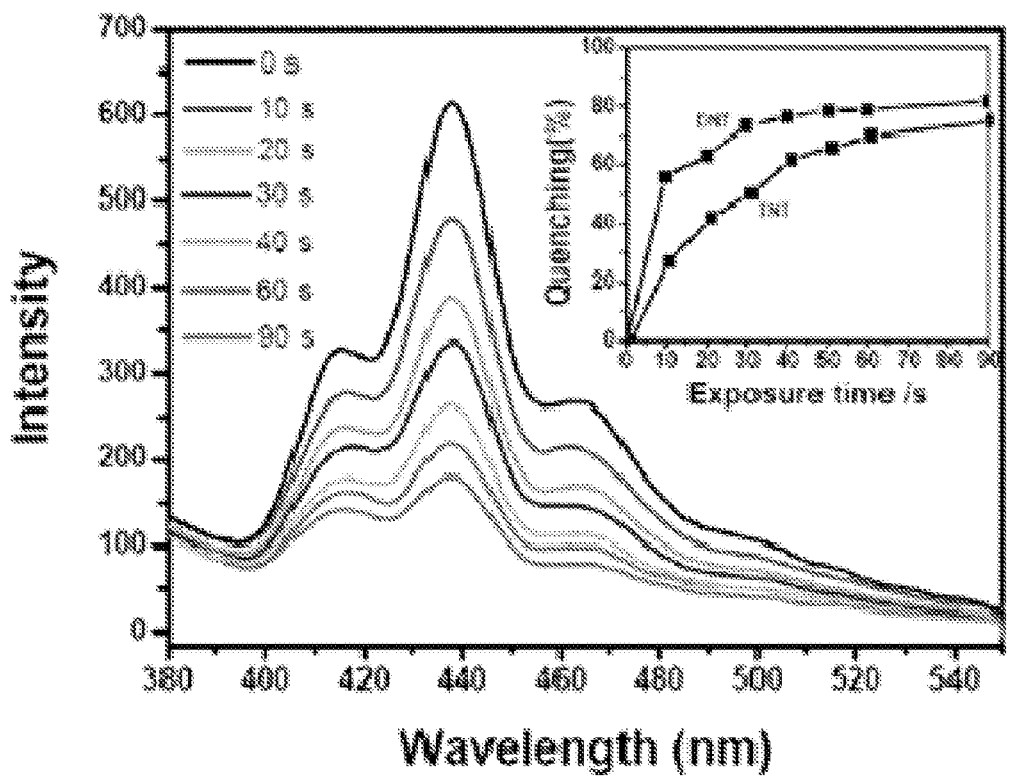
FIG. 4A is a fluorescence spectra of the nanofibril film upon exposure to TNT saturated vapor (5 ppb) at various time intervals. The inset shows the time-course of quenching for DNT and TNT vapor.

The continuous porous structure formed within the nanofibril film as depicted in FIG. 2A enables easy penetration and diffusion for gaseous molecules. This, in conjunction with the large surface area to volume ratio intrinsic to the small size of the nanofibrils, can result in expedient sample collection and thus enhanced vapor sensing. The 2,4-dinitrotoluene (DNT, 97%) and 2,4,6-trinitrotoluene (TNT, 99%) were purchased from Fisher and Chemservice, respectively. All other molecules and solvents (HPLC or spectroscopic grade) were purchased from Fisher or Aldrich, and used as received. Indeed, fast and efficient fluorescence quenching was observed for the nanofibril film when exposed to TNT and DNT vapor (FIG. 4A). The fluorescence quenching reached 50% and 70% after 30 and 60 s (respectively) of exposure to the saturated vapor of TNT (ca. 5 ppb). The same fluorescence quenching became much faster when exposed to the saturated vapor of DNT (FIG. 4A inset), for which 50% quenching took only 10 s. The faster response thus observed for DNT is likely due to its 20 times higher vapor pressure (ca. 100 ppb) compared to that of TNT.

Figure 4B:
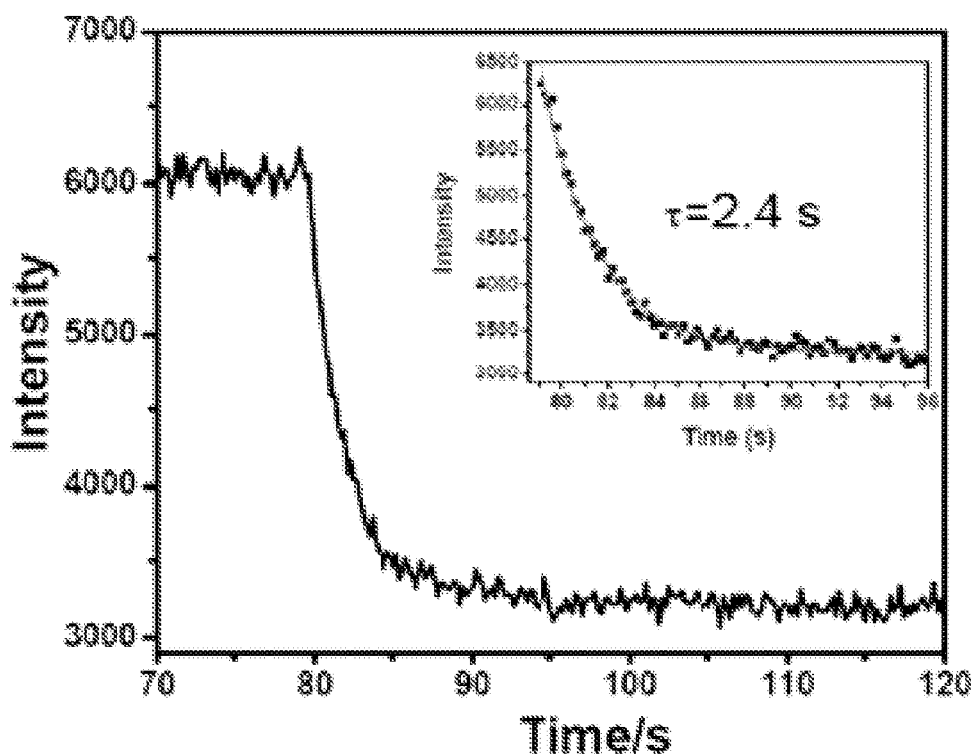
FIG. 4B shows time course of fluorescence quenching of the nanofibril film upon blowing over with saturated vapor of DNT, indicating a response time of 2.4 s. The intensity was monitored at 438 nm.
Figure 5:
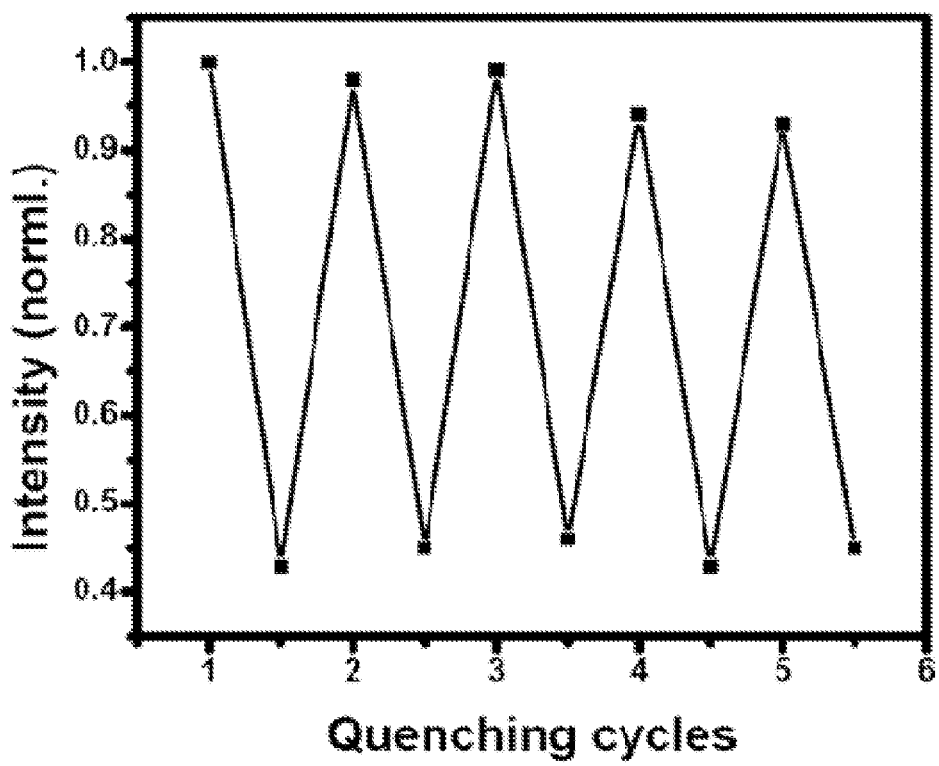
FIG. 5 shows five continuous quenching-recovery cycles as performed for the nanofibril film upon exposure to DNT. The quenching was performed by exposing the film to a saturated vapor of DNT for 30 s and the fluorescence was recovered by heating the film at 50° C. in a vacuum oven for 10 min.

To further explore the sensing response time, the fluorescence intensity of the nanofibril film was measured as a function of time before and after blowing over with saturated vapor of DNT (FIG. 4B). Fitting the intensity decay into a single exponential kinetics deduces a quick response time (defined as the decay lifetime) of 2.4 s for the quenching process (FIG. 4B inset). The fast response is conducive to practical application for onsite monitoring of explosive vapors. Moreover, the sensory materials are fully reversible. After tested with the explosives, the quenched fluorescence can be recovered simply by heating the film at 50° C. in a vacuum oven for 10 min. As shown in FIG. 5, over several repeated uses, the quenching efficiency remained nearly unchanged under the same testing conditions, implying high photostability of the film, which is desirable for organic sensors when considered for practical application.

Following the success on sensing of nitroaromatic explosives, the sensing capability of the nanofibril film over the nitroaliphatic explosives was also tested. Specifically, nitromethane was tested, which represents one of the highly volatile explosives (vapor pressure 36000 ppm), and still remains challenging for detection by current sensing techniques. This is likely due to the weak oxidizing power (i.e., low electron affinity) of nitromethane, particularly in comparison with the nitroaromatic compounds. The high volatility of nitromethane brings additional difficulty to vapor detection, for which strong interfacial binding (surface condensation) and sufficiently large surface area are usually demanded to achieve efficient sensing.

Figure 6A:
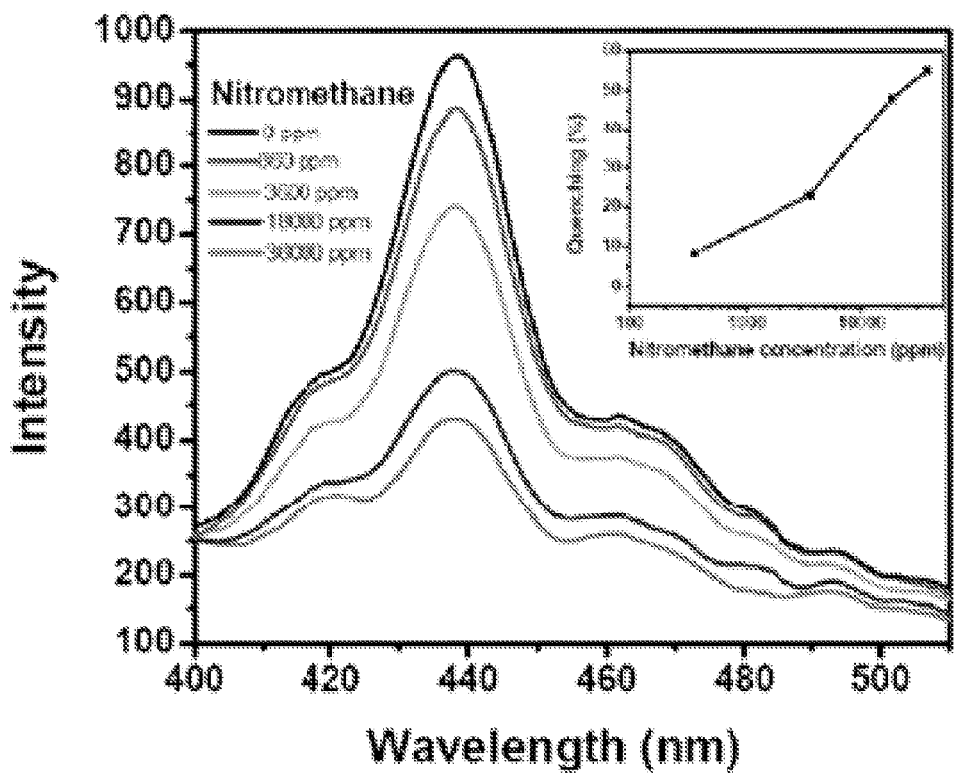
FIG. 6A is a fluorescence spectra of the nanofibril film upon exposure to various concentrations of nitromethane vapor. The inset shows the vapor concentration dependent quenching.

Because of its high volatility, the fluorescence quenching experiments of nitromethane were carried out in a sealed cell so as to maintain constant vapor pressure. Using this setup, the local vapor concentration could be continuously adjusted by injecting different amount of nitromethane vapor into the cell. The lowest vapor pressure reached in this case is about 1% dilution of the saturated vapor, corresponding to 360 ppm, at which about 8% fluorescence quenching was observed for the nanofibril film. With increasing the vapor pressure of nitromethane, the fluorescence quenching increases, reaching 55% under the saturated vapor of 36000 ppm (FIG. 6A).

Figure 6B:
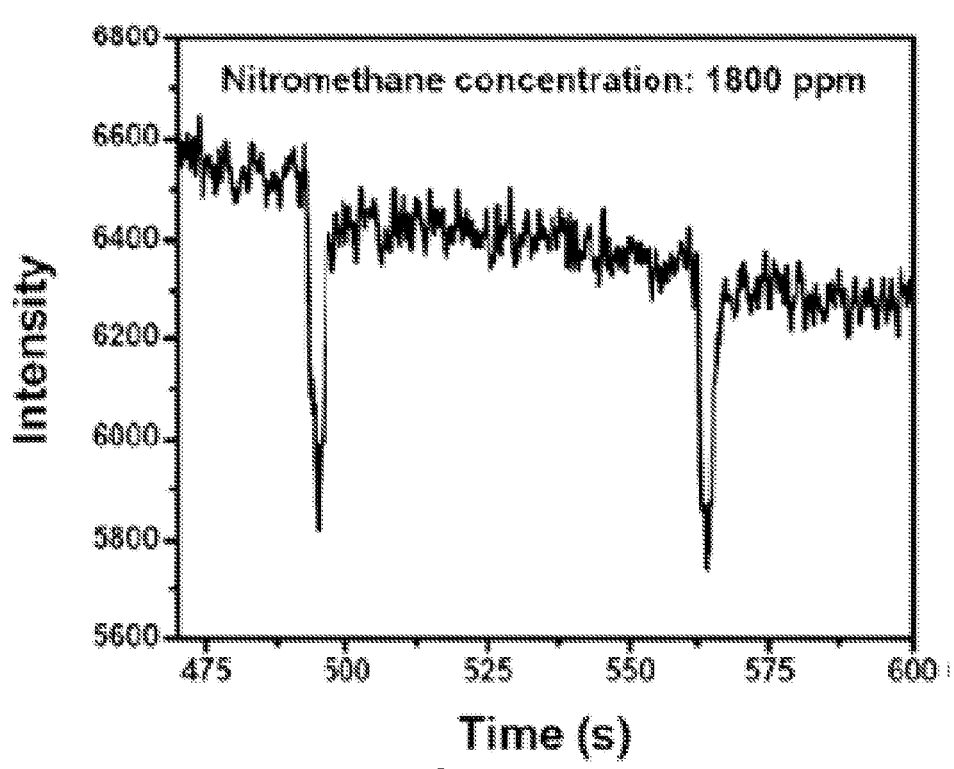
FIG. 6B shows time course of the fluorescence quenching upon blowing over with 1800 ppm nitromethane vapor.
Figure 7:
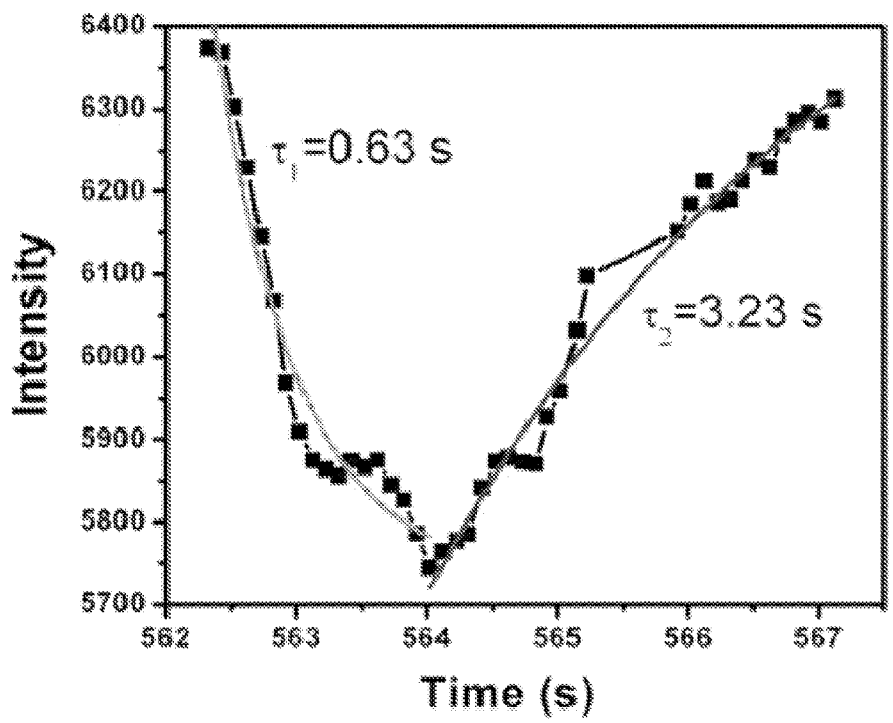
FIG. 7 shows fitting the fluorescence quenching and recovery process into a single exponential kinetics.

To explore the vapor sensing of nitromethane in open air, the nanofibril film was blew over with nitromethane vapor in different concentrations. Upon blowing at 1800 ppm (5% dilution from the saturated pressure), a significant fluorescence quenching (11%) was observed (FIG. 6B). Remarkably, the response was very fast and reversible. Fitting the intensity decay into a single exponential kinetics gives a response time of 0.63 s (FIG. 7). The fast response is highly favorable for applications where the sensor is used for onsite security monitoring. The effective vapor sensing obtained for nitromethane is at least partially due to the porous structure and large surface area to volume ratio of the nanofibril film, the combination of which enables efficient collection and accumulation of volatile molecules.

Figure 8:
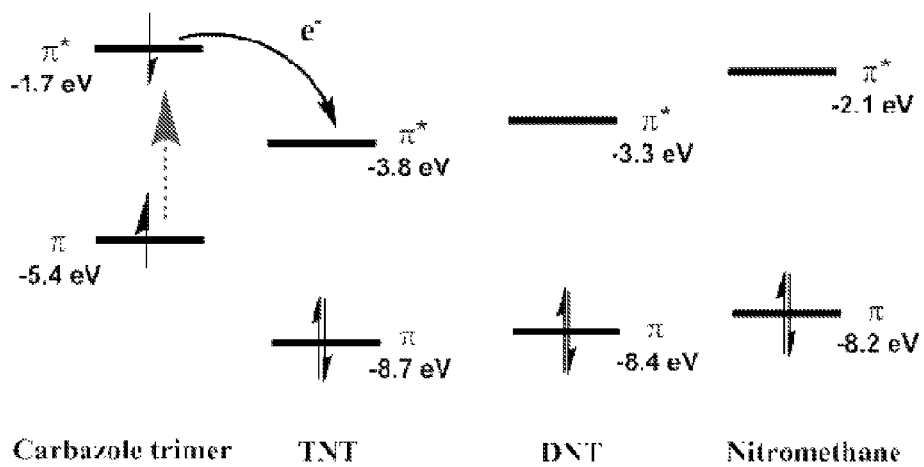
FIG. 8 are energy levels of HOMO ($\pi$) and LUMO ($\pi^*$) orbitals of the carbazole trimer, TNT, DNT and nitromethane showing the favorable driving force of electron transfer from the photoexcited state of carbazole to TNT (2.1 eV), DNT (1.6 eV) and nitromethane (0.4 eV). Geometry optimization and energy calculation were performed with density-functional theory (B3LYP/6-311g**) using Gaussian 03 package.
Figure 9A:
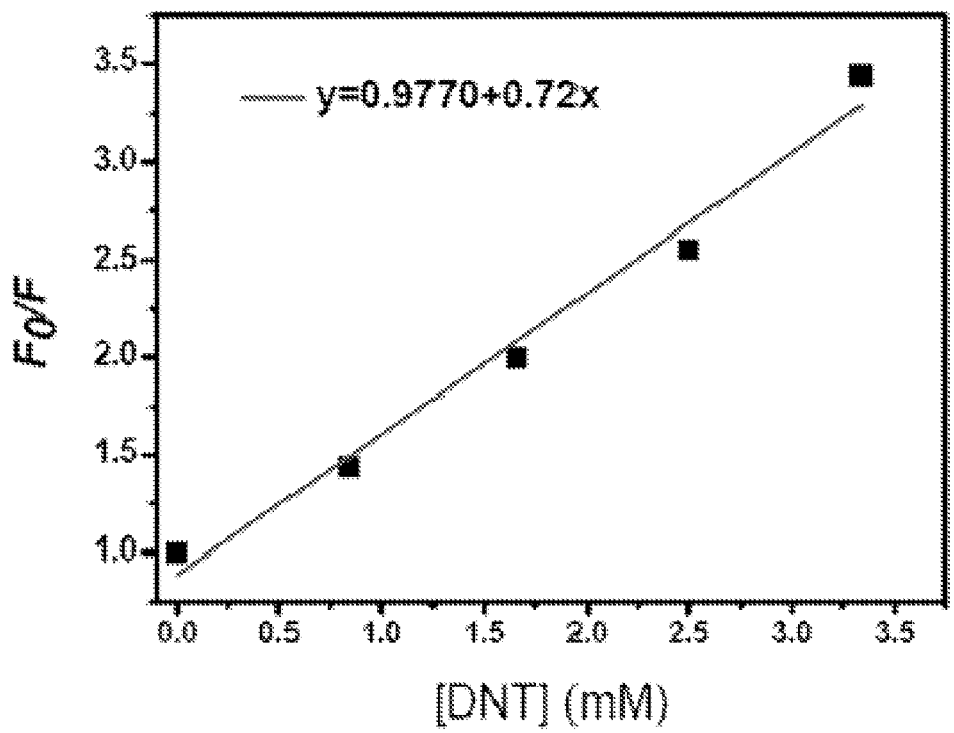
FIG. 9A is a Stern-Volmer plot for the fluorescence quenching of the carbazole trimer by DNT, giving a quenching constant of 720 $M^{-1}$.
Figure 9B:
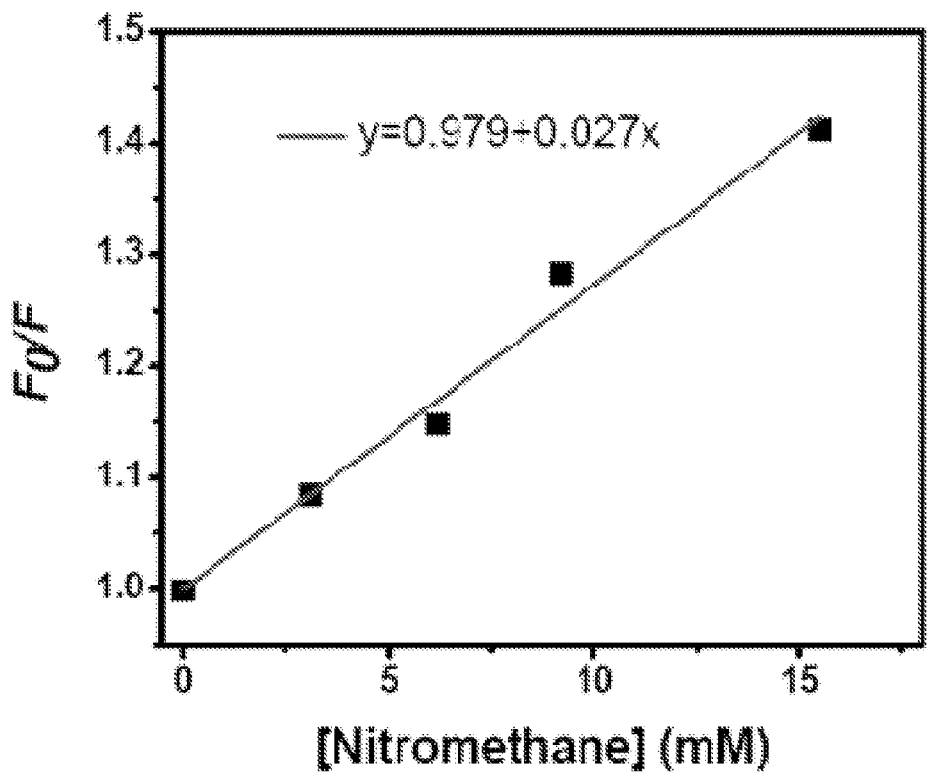
FIG. 9B is a Stern-Volmer plot for the fluorescence quenching of the carbazole trimer by nitromethane, giving a quenching constant of 27 $M^{-1}$.
Figure 10A:
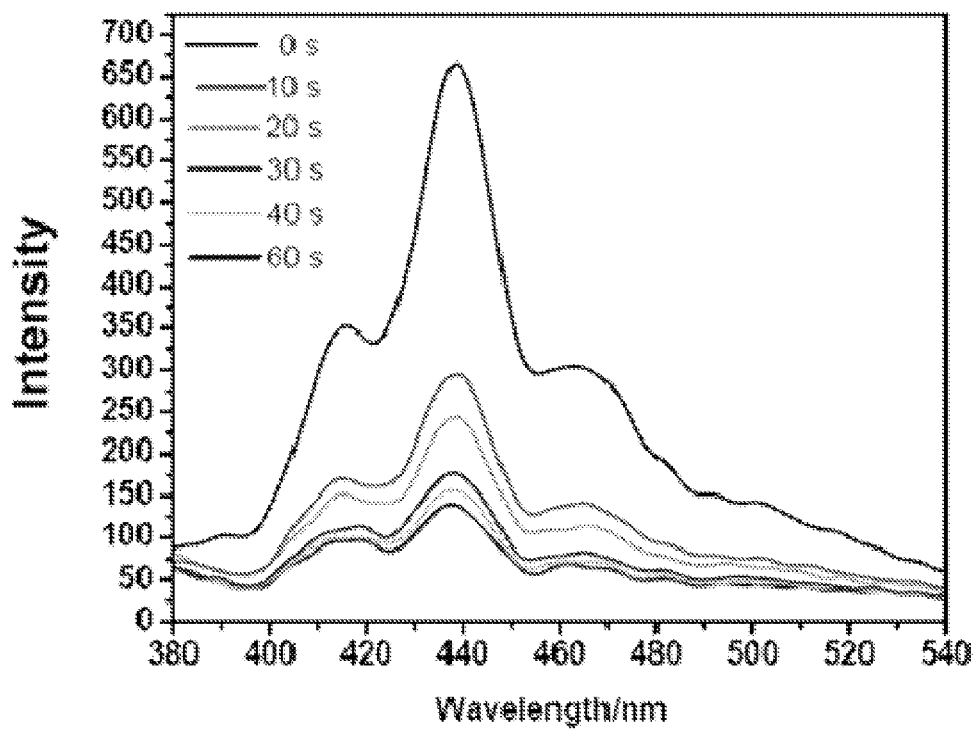
FIG. 10A is a fluorescence spectra of the nanofibril film upon exposure to DNT saturated vapor (100 ppb) at various time intervals.
Figure 10B:
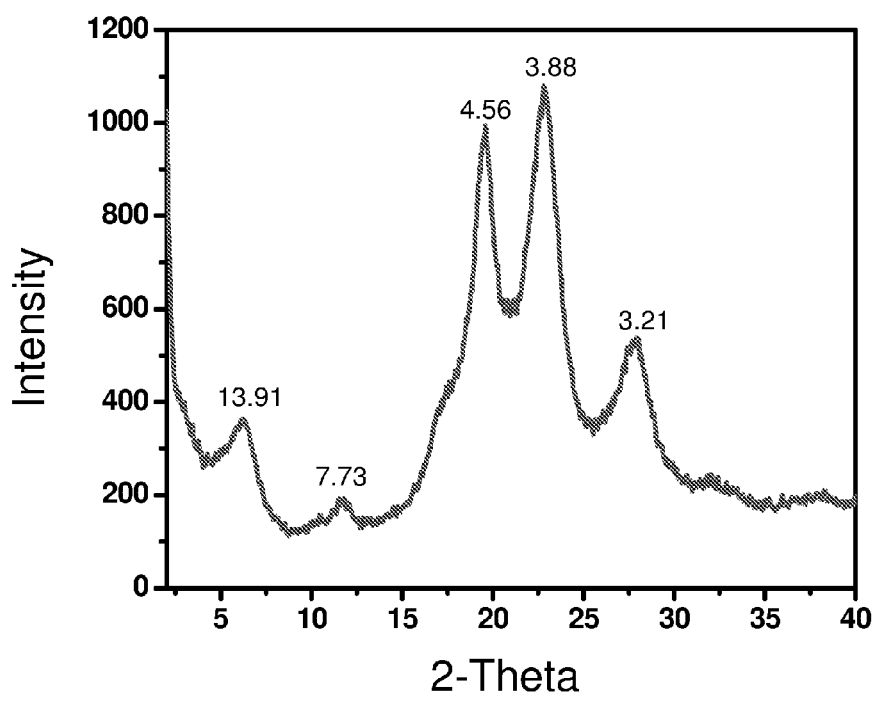
FIG. 10B is an XRD spectrum recorded from the nanofibrils. The d-spacings (Å) are labeled on the peaks.

The fluorescence quenching observed above can be attributed to the photoinduced electron transfer from the excited carbazole trimer (within the nanofibril) to the surface adsorbed explosive molecule (FIG. 8). Such an electron transfer is highly favored by the large driving force for TNT and DNT (2.1 eV and 1.6 eV, respectively). The driving force for nitromethane (0.4 eV) is significantly smaller, though still sufficient for affording an efficient electron transfer as indeed observed. The strong electron-donor-acceptor interaction between the carbazole trimer and the nitro-explosive molecules was also characterized by the steady state fluorescence quenching in solutions (FIGS. 9A and 9B), for which fairly large static quenching constants were obtained for DNT and nitromethane (720 $M^{-1}$ and 27 $M^{-1}$, respectively). Considering the intense effect of solvent, the quenching constant in gas phase should be significantly higher.

The time-dependent fluorescence quenching profile (FIGS. 4B, 6B and 7) was measured with an Ocean Optics USB4000 fluorometer, which can be switched to the mode to measure the emission intensity at a selected wavelength as a function of time.

In summary, fluorescent nanofibrils were fabricated from a 2,7-linked carbazole trimer. The film deposited from these nanofibrils demonstrated efficient vapor sensing for nitro-based explosives including TNT, DNT, and highly volatile nitromethane. The sensing mechanism relies primarily on the photoinduced electron transfer between the carbazole trimer and explosives, which is thermodynamically favorable by large driving force. The tunable porosity and large surface area to volume ratio intrinsic to the nanofibril film imply potential applications in sensor devices for infield explosives monitoring.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A fluorescence based sensor comprising:
   a) nanofibrils of a linear carbazole oligomer having the formula

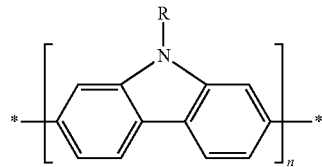

wherein n is 3 to 9, R are independently selected amine sidegroups, and at least one, but not all, R is a C1 to C14 alkyl; and
   b) a fluorescence detector.

2. The sensor of claim 1, wherein the at least one R is selected from the group consisting of linear alkyl, branched alkyl, cyclic alkyl, and combinations thereof.

3. The sensor of claim 1, wherein the at least one R is octyl.

4. The sensor of claim 1, wherein n is 3.

5. The sensor of claim 4, wherein a first R is H, a second R is octyl and a third R is H such that the linear carbazole oligomer is

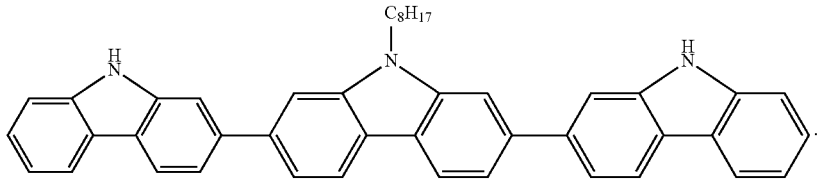

6. The sensor of claim 1, wherein at least one R is H.

7. The sensor of claim 1, wherein the nanofibrils have a diameter of about 10 nm to about 100 nm.

8. The sensor of claim 1, wherein the linear carbazole oligomer nanofibrils are formed as a film.

9. The sensor of claim 1, wherein the fluorescence detector is a fluorimeter.

10. A method of detecting explosives and quinones, comprising:
   a) exposing nanofibrils formed from a linear carbazole oligomer to a target sample, said linear carbazole oligomer having the formula

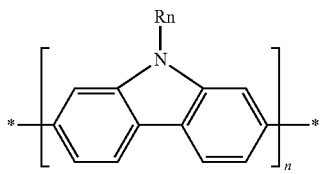

wherein n is 3 to 9, R are independently selected amine sidegroups, and at least one, but not all, R is a C1 to C14 alkyl; and
   b) measuring fluorescence responses of the linear carbazole oligomer nanofibrils.

11. The method of claim 10, further comprising displaying an explosives indicator based on the fluorescence responses.

12. The method of claim 11, wherein the explosives indicator is a quantitative measurement.

13. The method of claim 11, wherein the explosives indicator is a qualitative measurement.

14. The method of claim 10, wherein the at least one R is selected from the group consisting of linear alkyl, branched alkyl, cyclic alkyl, and combinations thereof.

15. The method of claim 10, wherein the at least one R is octyl.

16. The method of claim 10, wherein n is 3.

17. The method of claim 16, wherein a first R is H, a second R is octyl and a third R is H such that the linear carbazole oligomer is

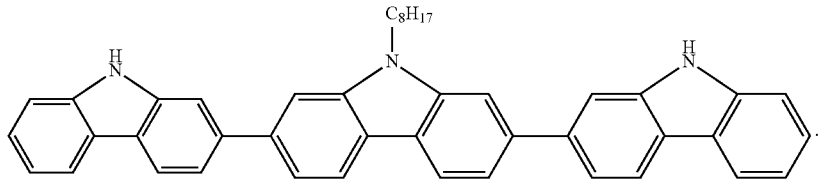

18. The method of claim 10, wherein at least one R is H.

19. The method of claim 10, wherein the linear carbazole oligomer nanofibrils have a diameter of about 10 nm to about 100 nm.

20. The method of claim 10, wherein the linear carbazole oligomer nanofibrils are formed as a film.

21. The method of claim 10, wherein the target sample is a nitroaromatic explosive or a nitroaliphatic explosive.

22. The method of claim 21, wherein the fluorescence responses are statistically significant at target sample concentrations of about 5 ppb and greater.

* * * * *